(12) United States Patent
Russell et al.

(10) Patent No.: US 9,465,013 B2
(45) Date of Patent: Oct. 11, 2016

(54) METHODS OF DETECTING AND IDENTIFYING MUNITIONS COMPOUNDS

(71) Applicants: Amber Lea Russell, Vicksburg, MS (US); Jennifer Maureen Seiter, Vicksburg, MS (US); Jessica Ann Coleman, Madison, MS (US); Anthony Joseph Bednar, Vicksburg, MS (US)

(72) Inventors: Amber Lea Russell, Vicksburg, MS (US); Jennifer Maureen Seiter, Vicksburg, MS (US); Jessica Ann Coleman, Madison, MS (US); Anthony Joseph Bednar, Vicksburg, MS (US)

(73) Assignee: THE UNITED STATES OF AMERICA AS REPRESENTED BY THE SECRETARY OF THE ARMY, Washington, DC (US)

( * ) Notice: Subject to any disclaimer, the term of this patent is extended or adjusted under 35 U.S.C. 154(b) by 12 days.

(21) Appl. No.: 14/223,595

(22) Filed: Mar. 24, 2014

(65) Prior Publication Data

US 2016/0011154 A1 Jan. 14, 2016

(51) Int. Cl.
*G01N 30/28* (2006.01)
*G01N 33/22* (2006.01)
*G01N 30/02* (2006.01)

(52) U.S. Cl.
CPC ............ *G01N 30/28* (2013.01); *G01N 33/227* (2013.01); *G01N 2030/027* (2013.01)

(58) Field of Classification Search
CPC ............... G01N 30/28; G01N 33/227; G01N 2030/027
USPC ......................................................... 73/61.56
See application file for complete search history.

(56) References Cited

U.S. PATENT DOCUMENTS

| | | | | |
|---|---|---|---|---|
| 4,252,537 A | * | 2/1981 | Cattran | G01N 30/02 210/656 |
| 4,749,656 A | * | 6/1988 | Ellerbe | G01N 30/96 210/662 |
| 6,477,907 B1 | * | 11/2002 | Chambers | G01N 1/2294 436/28 |
| 2009/0113982 A1 | * | 5/2009 | Hodyss | G01N 30/74 73/1.06 |

* cited by examiner

*Primary Examiner* — J M Saint Surin
(74) *Attorney, Agent, or Firm* — Brian C. Jones

(57) ABSTRACT

HPLC methods for detecting, identifying and quantifying munitions compounds or munitions materials are disclosed. Insensitive munitions explosives (IMX) can be detected along with conventional munitions compounds such as 2,4,6-trinitrotolene (TNT) in a single column analysis. The methods are also useful to provide analytical evaluation of soil samples, aqueous samples such as ground water samples and tissue samples containing insensitive munitions explosives (IMX).

20 Claims, 7 Drawing Sheets

METHODS OF DETECTING AND IDENTIFYING MUNITIONS COMPOUNDS

FIELD OF THE INVENTION

The invention relates to methods for detecting, identifying and quantifying munitions compounds or munitions materials. High performance liquid chromatography (HPLC) is used and new classes of munitions materials referred to as insensitive munitions explosives (IMX) can be defected along with conventional munitions compounds such as 2,4,6-trinitrotolene (TNT) in a single column analysis.

BACKGROUND OF THE INVENTION

The use of insensitive munitions explosives (IMX) is increasing as the U.S. Army and other armed forces seek to replace certain conventional munitions for improved soldier safety. The IMX formulations are more stable and less prone to accidental denotation while designed to match the performance of legacy materials. Two formulations of IMX are currently being produced; IMX 101 is qualified as a replacement for trinitrotoluene (TNT) in artillery rounds while IMX 104 is a replacement for composition B and may be used in mortar rounds.

The development of IMX compounds and then expanding use results in the need for a simple detection method for the four constituents of IMX-101 and 104; 2,4-dinitroanisole (DNAN), 3-nitro-1,2,4-triazol-5-one (NTO), 1-nitroguanidine (NQ), and Hexahydro-1,3,5-trinitro-1,3,5-triazine (RDX).

The standard environmental test method, U.S. EPA method 8330, for nitroaromatic, nitramine, and nitroester analysis of conventional munitions compounds uses high performance liquid chromatography (HPLC) separation and detection by ultra-violet absorption. The target analyte list for U.S. EPA method 8330 contains 17 components: 2-amino-4,6-dinitrotoluene, 4-amino-2,6-dinitrotoluene, 3,5-dinitroaniline, 1,3-dinitrobenzene 2,4-dinitrotoluene, 2,6-dinitrotoluene, Octahydro-1,3,5,7-tetranitro-1,3,5,7-tetrazocine (HMX), nitrobenzene, nitroglycerin, 2-nitrotoluene, 3-nitrotoluene, 4-nitrotoluene, [3-Nitrooxy-2,2-bis(nitrooxymethyl)propyl]nitrate (PETN), RDX, N-methyl-N2,4,6-tetranitroaniline(tetryl), 1,3,5-trinitrobenzene, 2,4,6-trinitrotoluene. Variations of this method can use electrospray ionization mass spectrometry (ESI-MS) or tandem mass spectrometry (MS-MS) for detection and quantitation of these constituents.

An alternative U.S. EPA method 8095, uses GC-ECD to quantify all of the target compounds m method 8330. However, three of the IMX constituents, NTO, NQ and DNAN, are not currently on the target analyte list of either EPA method 8330 or 8095. Of those three, only DNAN has been shown to be separated from concomitant compounds under the conditions of the U.S. EPA method 8330. In other words, neither U.S. EPA method 8330 nor U.S. EPA method 8095 has any effectiveness for separating NTO and/or NQ from concomitant compounds. Accordingly, both U.S. EPA method 8330 and U.S. EPA method 8095 are of little or no use when looking to provide analytical evaluation of soil samples, aqueous samples such as ground water samples and tissue samples containing insensitive munitions explosives (IMX).

There is currently a need for a simple method which efficiently separates and quantifies insensitive munitions constituents and legacy compounds on a single HPLC column. Previous work has focused on either the separation of individual IMX munitions constituents or the separation of one component and its derivatives. Consequently, the detection methods presently available utilize multiple columns for the analysis of IMX munitions constituents, thereby not only adding complexity but also extending the analysis time and cost of analysis.

Previous work has utilized a two column approach in order to quantify the individual components of the IMX family of compounds. The two column approach has been documented in dissolution studies of NTO from IMX compositions. The researchers used a Thermo Scientific Hypercarb column with an acidified eluent mixture for the analysis of the highly water soluble components, NQ and NTO, and a Dionex Acclaim® E1 column under EPA method 8330 conditions for the analysis of RDX and DNAN. The separation of NQ and DNAN in the presence of RDX has been demonstrated by ultrafast liquid chromatography. NTO and its derivatives have been analyzed by HPLC and capillary electrophoresis.

SUMMARY OF THE INVENTION

The present invention provides a streamlined HPLC-UV-ESI-MS technique for detection and quantification of IMX munitions constituents (MCs) in aqueous matrixes. The invention provides a single chromatographic separation and subsequent quantification of NQ, NTO, DNAN and RDX.

The invention provides methods which significantly reduce analysis time, solvent use, and costs for simultaneous detection of the analytes of interest and traditional explosive compounds. This streamlined method in accordance with the invention advances the field of analytical chemistry for detection of insensitive munitions and also may be has utility for the analysis of IMX munitions constituents from complex matrixes, such as ground water, soil, and tissue.

In certain embodiments of the invention, a liquid chromatographic method is provided for separation of mixtures comprising at least a first explosive compound and a second explosive compound, said method comprising the steps of: (a) providing a sample comprising at least said first and second explosive compounds, wherein said first explosive compound is a nitroaromatic and said second explosive compound is selected from the group consisting of nitroguanidine (HQ) and nitrotriazalone (NTO), (b) combining said sample with an initial acidic carrier solvent to form a sample solution, said initial acidic carrier solvent comprising less than about 99% by volume water and alcohol, or less than about 95% by volume water and alcohol, acetonitrile in an amount ranging from about 1% to about 5% by volume, or about 0% to about 5% by volume, and an acidic component, said initial acidic carrier solvent having an initial volume % water (and a corresponding initial volume % alcohol), based upon the composition of the initial acidic carrier solvent, (c) passing said sample solution through a liquid chromatography column, (d) continuously lowering said initial volume % water to a final volume % water (and a corresponding initial volume % alcohol), while continuing to pass acidic carrier solvent through said liquid chromatography column, such that a solvent gradient is established during said method, and (e) separating said at least two explosive compounds in said column. In the embodiment of the invention described in this paragraph, the nitroaromatic may be 2,4-dinitroanisole (DNAN) and the second explosive compound may have multiple components, such as nitroguanidine (NQ) and nitrotriazalone (NTO).

In other embodiments of the invention, a liquid chromatographic method is provided for separation of mixtures comprising at least a first explosive compound and a second explosive compound, said method comprising the steps of: (a) providing a sample comprising at least said first and second explosive compounds, wherein said first explosive compound is 2,4-dinitroanisole (DNAN) and said second explosive compound is selected from the group consisting of nitroguanidine (NQ) and nitrotriazalone (NTO), (b) combining said sample with an initial acidic carrier solvent to form a sample solution, said initial acidic carrier solvent comprising less than about 99% by volume water and alcohol, or less than about 95% by volume water and alcohol, acetonitrile in an amount ranging from about 1% to about 5% by volume, or about 0% to about 5% by volume, and an acidic component, said initial acidic carrier solvent having an initial volume % water (and a corresponding initial volume % alcohol), based upon the composition of the initial acidic carrier solvent, (c) passing said sample solution through a liquid chromatography column.
(d) continuously lowering said initial volume % water to a final volume % water (and a corresponding initial volume % alcohol), while continuing to pass acidic carrier solvent through said liquid chromatography column, such that a solvent gradient is established during said method, and (e) separating said at least two explosive compounds in said column. In the embodiment of the invention described in this paragraph, the wherein the second explosive compound may be nitrotriazalone (NTO), or alternately, the second explosive compound may be nitroguanidine (NQ) and die sample further comprises nitrotriazalone (NTO), or alternately the second explosive compound may be nitrotriazalone (NTO) and the sample may further comprise hexahydro-1,3,5-trinitro-1,3,5-triazine (RDX).

In any of the preceding embodiments of the invention, the alcohol may be methanol and the chromatographic method may be high performance liquid chromatography (HPLC). In any of the preceding embodiments of the invention, the initial volume % water may be in the range of from about 90% to about 80%, and the final volume % water may be in the range of from about 55% to about 45%. In any of the preceding embodiments of the invention, the corresponding initial volume % alcohol may be in the range of 9% to about 19%. In any of the preceding embodiments of the invention, the corresponding final volume % alcohol may be in the range of 44% to about 54%. In any of the preceding embodiments of the invention, the acidic component may be an organic acid, may be a halogenated organic acid, and in particular may be trifluoroacetic acid. In any of the preceding embodiments of the invention, said acidic carrier solvent may be 0.0005 to 0.0020 molar in said trifluoroacetic acid, or may be 0.0010 to 0.0015molar in said trifluoroacetic acid.

The methods of the invention may further comprise a step (f) of obtaining a quantitative measurement of an amount of said explosive compounds.

DETAILED DESCRIPTION OF THE INVENTION

Materials and Methods

Reagents and Supplies

Figure 1:
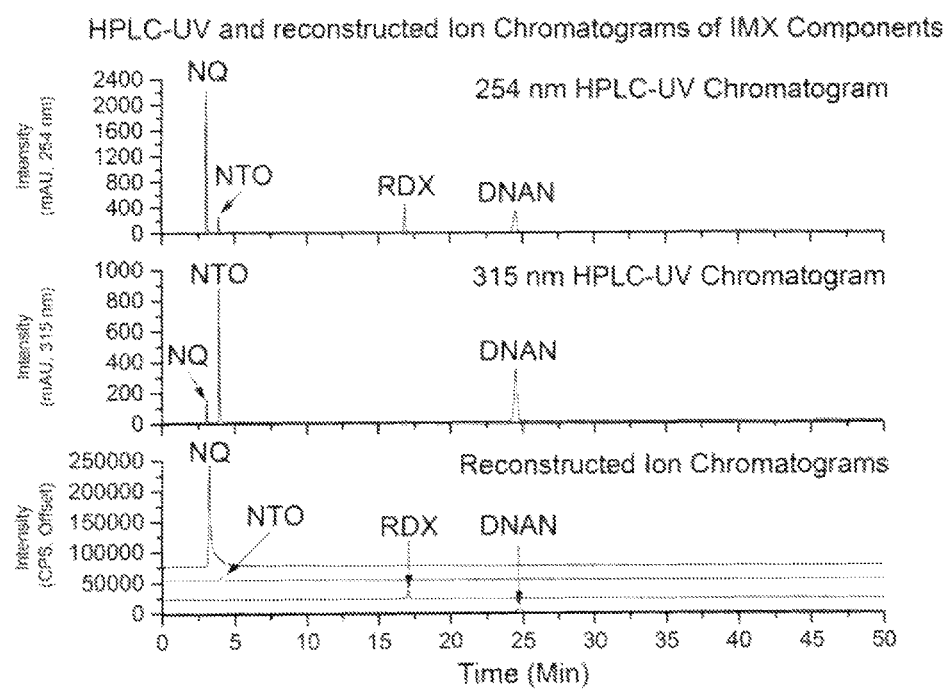
FIG. 1: HPLC-UV and Reconstructed Ion Chromatogram of IMX Components. The 254 nm (top) and 315 nm (middle) UV traces and reconstructed ion chromatograms (bottom) of NQ (m/z 105, [M+H]$^+$), NTO (m/z 131, [M+H]$^+$), RDX (m/z 245, [M+Na]$^+$) and DNAN (m/z 199, [M+H]$^+$) at 10 mg/L analyzed by HPLC-UV-ESI-MS.

All commercially available chemicals used were of analytical grade or higher purity and were used without further purification. Methanol and acetonitrile (ACN) were purchased from JT Baker (Phillipsburg N.J.). DNAN was purchased from Alfa Aesar (Ward Hill, Mass.). RDX, NQ, EPA mix A, and EPA mix B were purchased from SigmaAldrich (St. Louis, Mo.). Military grade crystalline NTO, IMX 101 and 104 were supplied by BAE Systems (Holston Army Ammunition Plant, Tenn.) and used without further purification. 18.3 MΩ cm deionized (DI) water was used for all experiments. Mixed analyte calibration standards containing EPA 8330 analytes at 1000 mg/L were purchased from Supelco (St. Louis, Mo.). Working calibration standards were prepared by volumetric dilutions of the stock explosive standard with 18.3 MΩ cm DI water.

Sample Preparation

All samples were prepared in DI water unless otherwise stated and analyzed by the HPLC-UV method in accordance with embodiments of the present invention. The method in accordance with embodiments of the invention comprises an acidified eluent. The method in accordance with embodiments of the invention also utilizes an acidified eluent gradient that ramps downward, and in certain embodiments of the invention, as illustrated, the acidified eluent gradient ramps downward from 86 to 51% aqueous.

In contrast to the invention, samples analyzed by EPA 8330 are prepared in 50:50 water:ACN. However, it has been surprisingly discovered that ACN adversely affects the chromatography of early eluting compounds (NQ and NTO) analyzed by the method in accordance with embodiments of the present invention.

The effect of ACN concentration on the chromatography of NTO is discussed in further detail below. In using the method in accordance with embodiments of the present invention, there was no notable consequence of ACN concentration In the sample on the traditional EPA 8330 (non IMX) analytes.

Instrumentation

HPLC analysis was conducted using an Agilent (Palo Alto, Calif.) 1200 HPLC equipped with either a Phenomenex Synergi 4-μm hydroRP or a Restek Pinnacle II biphenyl reversed-phase column. The latter reversed-phase column may be used as the second column for analyte confirmation when MS confirmation is not used. Mass spectrometric analysis was carried out using a Bruker Daltonics Inc. (Billerica, Mass.) Esquire 6000 ion trap mass spectrometer equipped with an electrospray ion (ESI) source. The operating conditions for the HPLC and the MS are described in Table 1 as is the HPLC gradient program.

TABLE 1

Instrumentation and operating conditions for HPLC-UV and ESI-MS analysis.

| HPLC |
| Agilent 1200 system with quaternary pump |

| | |
|---|---|
| RP Column 1 | Phenomenex Synergi 4-μm hydroRP; 80A 250 × 4.6 mm |
| RP Column 2 | Restek Pinnacle II biphenyl; 5 μm, 150 × 4.6 mm |
| Autosampler and Column temperatures | 10° C. and 25° C., respectively |
| Mobile phase flow rate | 1 mL/min |
| UV absorbance wavelenghts | 254 nm & 315 nm |
| Injection volume | 50 μL |
| Total chromatogram time | 45 min |

Elution program and mobile phase

| Time (min) | DI Water | ACN | 0.1% TFA | MeOH |
|---|---|---|---|---|
| 0 | 76% | 4% | 10% | 10% |
| 5 | 76% | 4% | 10% | 10% |
| 10 | 41% | 4% | 10% | 45% |
| 35 | 41% | 4% | 10% | 45% |
| 40 | 76% | 4% | 10% | 10% |
| 45 | 76% | 4% | 10% | 10% |

ESI-MS
Bruker Esquire 6000

| | |
|---|---|
| Capillary potential | −850 V, 7 nA |
| Nebulizer gas | 50 psi |
| Dry gas | 10 psi |
| Dry gas temperature | 150° C. |
| Skimmer | 40 V |
| Nitroguanidine (NQ) Quantitation mass monitored, Retention Time | 105 m/z, $[M + H]^+$, 3 min |
| Nitrotriazalone (NTO) Quantitation mass monitored, Retention Time | 131 m/z, $[M + H]^+$, 4 min |
| 2,4-dinitroanisole (DNAN) Quantitation mass monitored, Retention Time | 199 m/z, $[M + H]^+$, 24.3 min |
| Hexahydro-1,3,5-trinitro-1,3,5 triazine (RDX) Quantitation mass monitored, Retention Time | 245 m/z, $[M + Na]^+$, 16.2 min. |

TABLE 1-continued

Instrumentation and operating conditions for HPLC-UV and ESI-MS analysis.

| ESI-MS CID | |
|---|---|
| Isolation width | 4 mass units |
| CID amplitude | 0.5 V |

TABLE 2

Retention times and compound identification for 5 mg/L 17 component mixed explosive standard (shown in FIG. 3) analyzed with a Phenomenex Synergi 4-μm hydroRP column. The IMX constituents are shown in bold.

| Chromatographic Peak | RT | Compound |
|---|---|---|
| 1 | 3.0 | NQ; 1-nitroguanidine |
| 2 | 4.0 | NTO; 3-nitro-1,2,4-triazol-5-one |
| 3 | 14.3 | HMX; Octahydro-1,3,5,7-tetranitro-1,3,5,7-tetrazocine |
| 4 | 16.2 | RDX; Hexahydro-1,3,5-trinitro-1,3,5-triazine |
| 5 | 18.1 | 1,3,5-TNB; 1,3,5-trinitrobenzene |
| 6 | 21.2 | Tetryl; N-methyl-N,2,4,6-tetranitroaniline |
| 7 | 22.5 | 1,3-DNB; 1,3-dinitrobenzene |
| 8 | 22.9 | NB; nitrobenzene |
| 9 | 23.5 | 2,4,6-TNT; 2,4,6-trinitrotoluene |
| 10 | 24.3 | DNAN; 2,4-dinitroanisole |
| 11 | 25.8 | 4-Am-DNT; 4-amino-2,6-dinitrotoluene |
| 12 | 26.4 | 2-Am-DNT; 2-amino-4,6-dinitrotoluene |
| 13 | 28.4 | 2,6-DNT; 2,6-dinitrotoluene |
| 14 | 28.9 | 2,4-DNT; 2,4-dinitrotoluene |
| 15 | 33.5 | 2-NT; 2-nitrotoluene |
| 16 | 35.2 | 4-NT; 4-nitrotoluene |
| 17 | 37.2 | 3-NT; 3-nitrotoluene |

Calibration

The calibration curve for the HPLC-UV-MS used mixed analyte standards with concentrations of 0.005, 0.01, 0.05, 0.1, 0.5, 1, 5, 10, 25, 50 and 100 mg/L. The UV linear correlation coefficients (Pearson's r) of the linear regression lines drawn between the peak area and the concentration were at 0.98 or greater when all 11 calibration standards are included.

The instrument calibrations were verified using second analytical preparations of 25 and 1 mg/L standards, recoveries were required to be within ±20% of the nominal concentrations. Continuing calibration verification (CCV) standards were analyzed at a frequency of 5% and bracketed the samples for each analytical batch; the analyte recoveries for the CCVs were required to be within ±10% of the nominal concentrations.

Standard Chromatograms and Detection Limits

Figure 2:
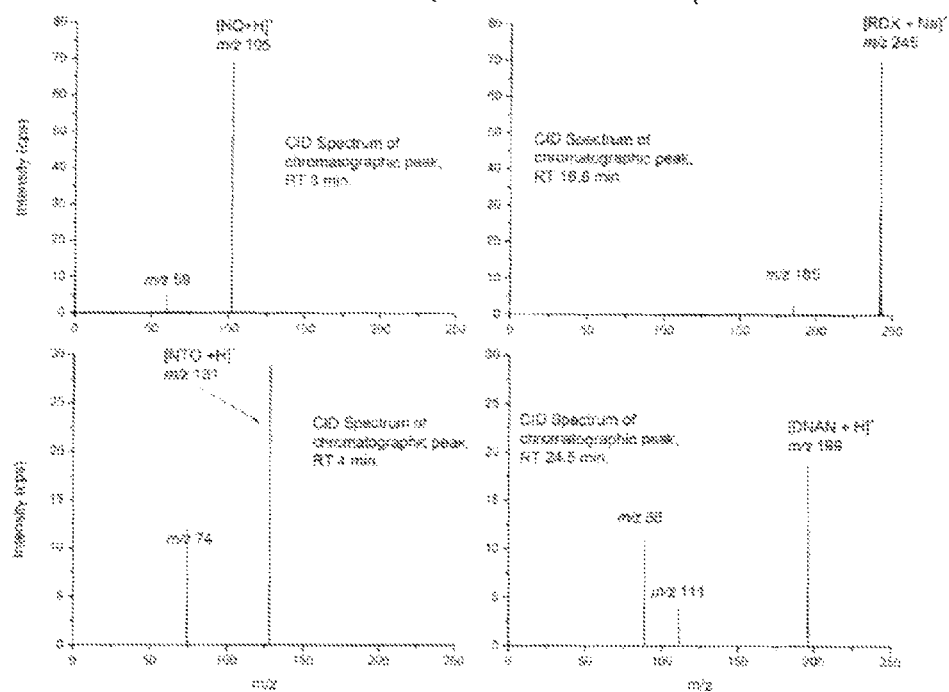
FIG. 2: Positive Ion CID Mass Spectra of IMX Components. CID mass spectra of the four UV chromatographic peaks identified in the analysis of a 10 mg/L IMX mixed standard, (shown in FIG. 1). The compounds of interest, NQ, RDX, DNAN, and NTO (clockwise from top left), are identified.

The HPLC-UV-ESI-MS analysis method in accordance with embodiments of the present invention showed excellent separation between DNAN, RDX, NTO, and NQ on the single column method described. The retention times for the IMX munitions constituents are given in Table 1 for the Phenomenex Synergi column. FIG. 1 shows the separation of IMX components NQ, NTO, RDX and DNAN from the analysis of a 10 mg/L standard. Two wavelengths were used, in certain embodiments, for optimal detection of all analytes. An advantage of the method in accordance with embodiments of the present invention is that the insensitive munitions explosives (IMX) components are easily separated from the solvent void volume and each other. The reconstructed positive ion chromatograms for the ions of interest (m/z 105 (NQ+H), 131 (NTO+H). 199 (DNAN+H) and 245 (RDX+Na)) axe also shown in FIG. 1. The reconstructed ion chromatograms were offset for clarity. Collision induced dissociation (CID) mass spectra (FIG. 2) of the four chromatographic peaks, shown in FIG. 1, show characteristic ions for the four constituents of IMX to use as absolute compound identification. The ion of m/z 105 ([NQ+H]$^+$) shows a CID loss of 46 (—NO$_2$) resulting in a fragment ion of m/z 59. The CID of the ion of m/z 199 ([DNAN+H]$^+$) yields two fragment ions of m/z 111 (loss of 88) and 88 (loss of 111). CID of the ion of m/z 131 ([NTO+H]$^+$) yields an ion of m/z 74 (loss of 57). CID of the sodiated molecular ion of RDX (m/z 245) shows a loss of 60 resulting in an ion of m/z 185. RDX is also obeservered as a sodium bound dimer (m/z 467, not shown), which undergoes the loss of 222 (RDX) open CID. The IMX constituents were easily identified using these spectra which can be used to confirm the identity of components in mixed samples.

Figure 3:
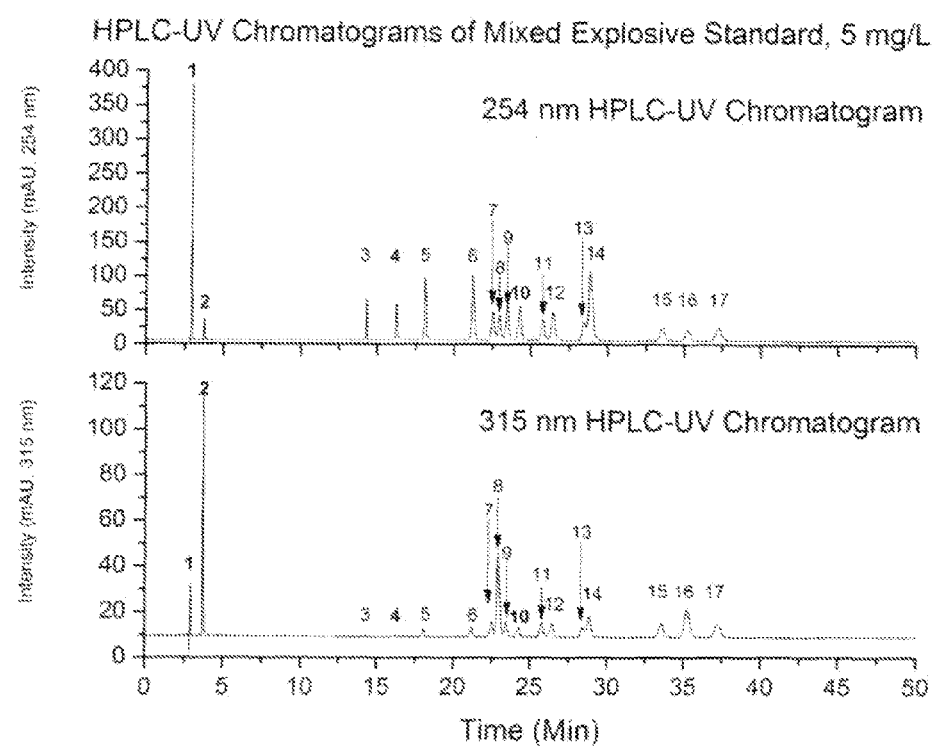
FIG. 3: HPLC-UV Chromatograms of Mixed Explosive Standard, 5 mg/L. 254 nm and 315 nm absorbance trace chromatograms of NQ, NTO, RDX, DNAN and 13 other common explosive compounds at 5 mg/L analyzed by HPLC-UV. NQ, NTO, RDX and DNAN are shown in bold.

In the method in accordance with embodiments of the present invention, analysis of NQ, NTO and DNAN in the presence of 14 common explosive analytes (HMX, RDX, 1,3,5-TNB, 1,3-DNB, Tetyl, NB, 2,4,6-TNT, 4-Am-DNT, 2-Am-DNT, 2,4-DNT, 2,6-DNT, 2-NT, 3-NT, and 4-NT resulted in separation of all 17 components (FIG. 3). Commercially available standards, EPA 8330 mix A and B (Sigma-Aldrich, PN 47283 and 47284), were used to prepare the mixture of the 14 common explosives. A typical HPLC-UV chromatogram for a mixed calibration standard containing 5 mg/L of the 4 IMX constituents investigated and the 13 additional common explosive compounds is shown in FIG. 3. RDX is present in both the IMX constituents and the mixture of the 14 common analytes. The identities and retention time of the 17 chromatographic peaks, observed in FIG. 3, is given in Table 2.

Figure 4:
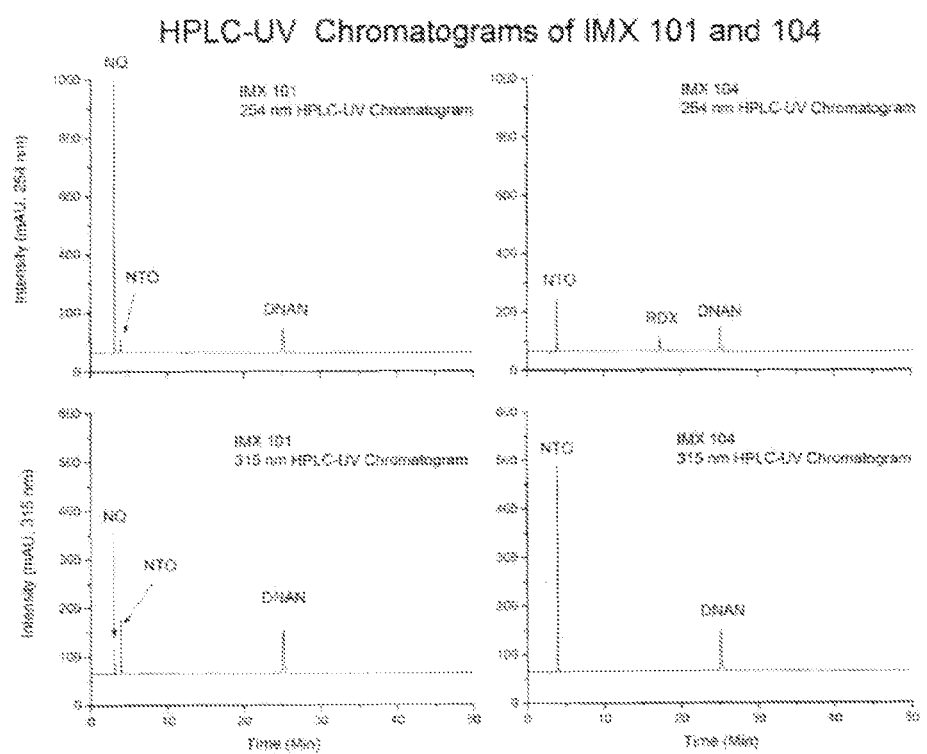
FIG. 4: HPLC-UV Chromatograms of IMX 101 and 104 analyzed with a Phenomenex Synergi 4-µm hydroRP column. HPLC-UV chromatograms of 3.0 mg/L IMX 101 (left) and 104 (right) samples. UV absorbance at 254 (top) and 315 nm (bottom) was monitored for detection. IMX 101 and 104 were dissolved in 100% DI water.

UV chromatograms obtained by the method in accordance with embodiments of the present invention of 30 mg/L IMX 101 and 104 solutions are shown in FIG. 4. Solid samples of IMX 101 and 104 were dissolved by stirring in DI water for 24 hours. The resultant solutions were filtered and analyzed by HPLC-UV under the method conditions method in accordance with embodiments of the present invention given in Table 1.

In general, the HPLC method in accordance with embodiments of the present invention achieves the separation of NQ, NTO, DNAN and RDX in a single analysis in a single column. The method in accordance with embodiments of the present invention utilizes both an acidified mobile phase, and an acidified mobile phase gradient, detailed above for a particular embodiment in Table 1.

TABLE 3

Method Detection limits (MDLs) determined from eight replicate analyses at 0.050 mg/L, and analyte recoveries of a 0.010 mg/L verification sample using the single column HPLC analysis method. Percent recovery (% REC) and percent relative standard deviation (% RSD) determined from eight laboratory control sample (LCS) and matrix spike sample (MS) replicate analyses at 2 mg/L using the single column HPLC analysis method.

| Analyte | Calculated MDL (mg/L) n = 8 | Measured concentration of 10 µg/L verification sample | Verification Sample % REC | LCS % REC n = 8 | LCS % RSD n = 8 | MS % REC n = 8 | MS % RSD n = 8 | QSM |
|---|---|---|---|---|---|---|---|---|
| NQ | 9 | 10 | 104.9 | 93.7 | 13.4 | 100.9 | 7.2 | |
| NTO | 7 | 11 | 106.4 | 104.2 | 16.5 | 100.5 | 17.0 | |
| RDX | 8 | 11 | 109.4 | 89.0 | 17.3 | 86.1 | 30.3 | 50-160 |
| DNAN | 8 | 9 | 93.3 | 102.0 | 15.3 | 98.9 | 17.9 | |

Method Detection Limits

Method detection limits (MDLs) for the IMX compounds were determined for the HPLC method in accordance with embodiments of the present invention as described in 40 CFR Part 136 [11], and are listed in Table 3. Briefly, eight 1 mL volumes of DI water were fortified with the analytes of interest at a concentration of 0.050 mg/L and analyzed using the HPLC method described. The MDL was calculated by multiplying the standard deviation for each set of replicates by a factor of 3. A ninth sample was fortified at 0.010 mg/L, roughly the calculated MDL for the four IMX analytes, and used as the verification sample.

DI water was used as a method blank; no analytes were detected in any of the blank analyses above the MDL. The MDL's ranged from 7 µg/L (NTO) to 9 µg/L (NQ) and are on the order of MDL's observed for other common explosives analyzed by similar methods. A laboratory control sample (LCS) was analyzed with a method blank with each batch of samples. The LCS was prepared by fortifying reagent water with all the analytes of interest at concentrations approximately one half highest calibration standard.

The Department of Defense (DoD) Quality Systems Manual (QSM) (2009) only lists recoveries for one of the analytes of Interest, RDX. However, in the absence of specific guidance from the DoD QSM (2009), the recoveries of the mid-level LCSs in Table 4 were consistent with the acceptance ranges for other MC's in the DoD QSM (2009), which range from 45 to 160% recovery.

Matrix spike (MS) and MS duplicate (MSD) analyses were performed on water samples that had been exposed to Memphis silt soli [14-15] and then filtered (0.45 µm Whatman GD/XP filter) prior to 2 mg/L fortification with the analytes of interest (NQ, NTO, RDX and DNAN) and analysis. The average of 8 MS recoveries, Table 3, generally fell within the acceptance ranges, 80-120%, for the mid-level LCSs. The QSM [16] limits for RDX are also given in Table 3. The relative percent differences (RPDs) between replicates were generally less than 20% with the exception of RDX which had a RPD of 30.3 for the matrix spike samples.

River water samples were also collected from the Yaxoo River (Vicksburg, Miss.) and filtered prior to fortification with the analytes of interest and analysis. Aliquots filtered with glass wool and 0.45 μm GD/XP were fortified at a concentration of roughly twice the defection limit (0.020 mg/L) prior to analysis. Recoveries for the glass wool filtered NQ, NTO, RDX, and DNAN were 95.9, 117.9, 99.8 and 84.1 respectively. The recoveries for the 0.45 μm filtered river water sample were 94.8, 123.1, 118.0, and 106.9 for NQ, NTO, RDX, and DNAN respectively.

An aliquot of the 0.45 μm filtered 0.02 mg/L fortified sample diluted 50:50 with MeOH was also prepared, to further demonstrate effect of added solvent on natural matrices. Recoveries for NQ, NTO, RDX, and DNAN were 101.1, 90.7, 107.7 and 114.9 respectively from the sample split with MeOH.

Effect of ACN and MeOH in Sample Preparation

In accordance with embodiments of the present invention, higher percentages of water in the initial eluent result in greater separation of NQ and NTO from the void volume and each other. In embodiments of the invention, starting eluent conditions of 86% DI water, 4% ACN, and 10% 0.1% TFA result in the following analyte retention times; NQ, 4.5 min, NTO, 7 min, RDX, 21 min, DNAN, 24.5 minutes.

However, solvents such as methanol and acetonitrile, are often used to extract munitions from ground water, soil, sediment and tissue. Solid phase extraction (SPE) of munitions from water, for example, results in compounds dissolved in ACN, which are then diluted with DI water for analysis by traditional method 8330.

Consequently, the tolerance of the newly developed method in accordance with embodiments of the present invention to ACN and or MeOH is of great importance.

Figure 5:
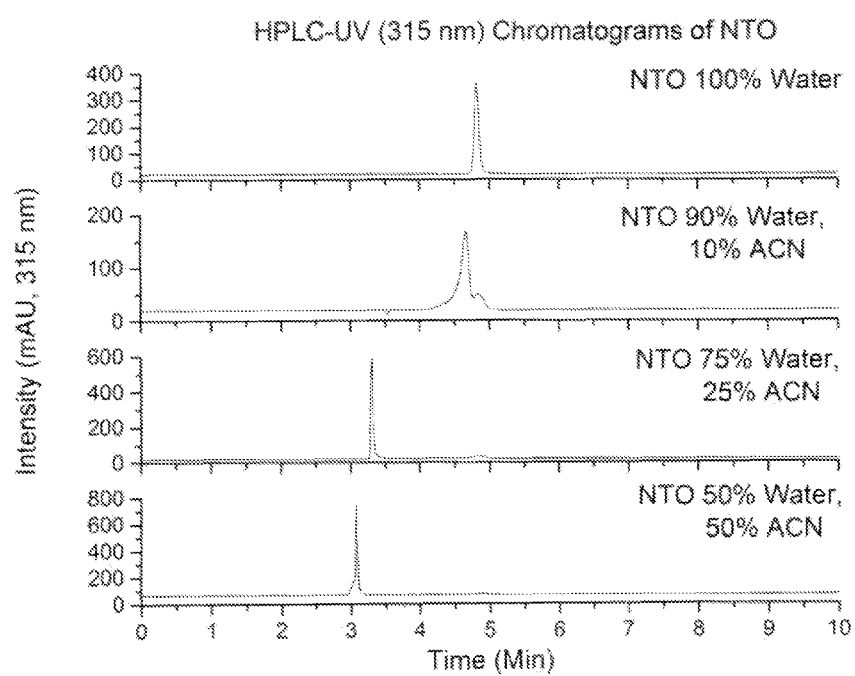
FIG. 5: HPLC-UV (315 nm) Chromatograms of NTO. UV chromatograms (315 nm) of 5 mg/L NTO samples at various ACN concentrations analyzed by HPLC-UV. The NTO chromatographic peak shifts significantly with increasing ACN.

Analysis of the compounds of interest in 50:50 water: ACN showed no change for DNAN and RDX compared to the dissolved standards in 100% water, however the chromatography of the more hydrophilic NTO, deteriorated significantly. The effects of acetonitrile concentration on the chromatographic peak shape and retention time of NTO are shown in FIG. 5. The peak shape deteriorates rapidly and results in a nearly two minute chromatographic retention time shift. Increasing the solvent concentration of the starting eluent composition did not mitigate these effects for samples containing ACN. However, the addition of methanol, 10%, to the starting HPLC gradient conditions in accordance with embodiments of the present invention decreased these shifts and changes to peak shape. The addition of solvent (MeOH or ACN) to the initial eluent composition increases the elution strength and results in shorter retention times. The ACN shifts the equilibrium distribution of the NTO analyte between mobile and stationary phases such that retention time is reduced and the peak shape is deteriorated. MeOH does not appear to change the equilibrium distribution as significantly; possibly due to methanol's lower elution strength compared to that of ACN. The result is that methanol does not have as strong an effect on the peak shape and virtually no retention time shift for NTO, as shown in the top and middle chromatograms of FIG. 6.

Figure 6:
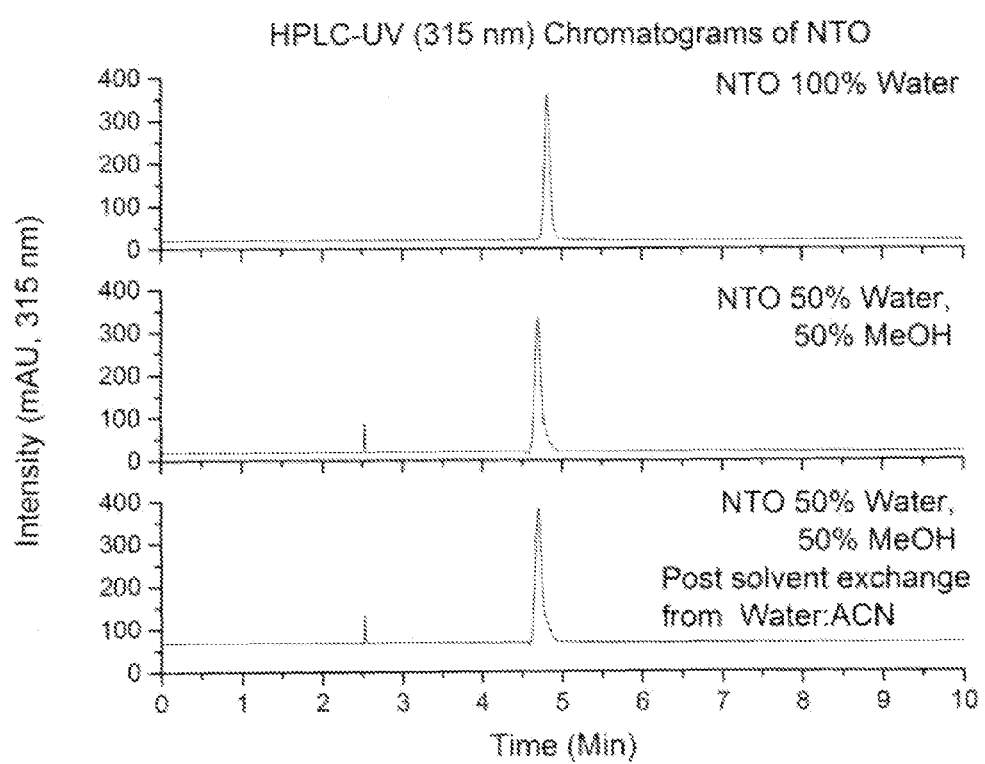
FIG. 6: HPLC-UV (315 nm) Chromatograms of NTO. UV chromatograms (315 nm) of 5 mg/L NTO samples analyzed by HPLC-UV. The top chromatogram is a 5 mg/L NTO sample in 100% DI water. The middle chromatogram is a 5 mg/L NTO in 50:50 MeOH and DI water. The bottom chromatogram is a 1 mL 5 mg/L NTO sample that was prepared in 50:50 ACN:DI water, evaporated under nitrogen to 0.5 mL and then brought to a final volume of 1 mL with methanol.

The bottom chromatogram, of FIG. 6, shows the result of evaporating a 5 mg/L 1 mL sample of NTO, prepared in 50:50 ACN; water, under nitrogen to 0.5 mL and adjusting to a final volume, of 1 mL with methanol prior to HPLC-UV analysis in accordance with embodiments of the present invention. The solvent exchange resulted in 95% recovery of NTO, and may represent a viable amelioration strategy of the retention time shift for application of this method in accordance with embodiments of the present invention to organic solvent used to extract IMX constituents from solid matrices (e.g. soils or tissues).

Figure 7:
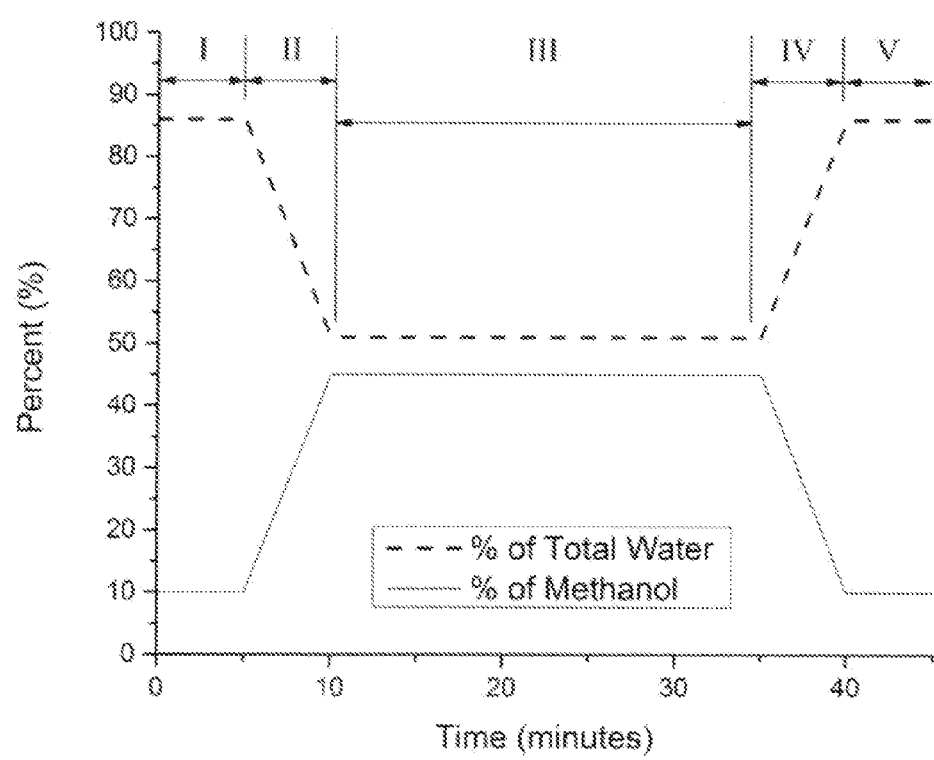
FIG. 7: Shows of the eluent concentrations of alcohol and water plotted against time and also shows the gradient changes in solvent concentration for certain embodiments of the invention.

A further description of the process in accordance with certain embodiments of the invention for separating mixtures of explosive compounds may refer to Table 1, Instrumentation and Operating conditions for HPLC-UV and ESI-MS analysis, in particular, the elution program and the mobile phase. Such a description may also refer to FIG. 7, which graphically depicts the elution program in a more general way. It is noted, in embodiments of the invention, that there may be at least three distinct portions of the elution program. FIG. 7 shows both percent of total water and percent of total methanol as a function of time in certain embodiments of the invention. In the following paragraphs, the invention is described in terms of the percent of total water, also described as ratio of water to alcohol. It is equally possible to describe the invention in respect of the lower line in FIG. 7, i.e., with respect to the percent of methanol.

In certain embodiments of the invention, the concentration of TFA and ACN may stay constant throughout the separation in accordance with the invention.

In a first portion of FIG. 7 (depleted by Roman numeral I) of the process in accordance with certain embodiments of the invention, the ratio of water to alcohol is greater than 3:1 by volume, and may be as high as 10:1. In certain embodiments of the invention, the ratio of water to alcohol in said first portion of the process is between about 7:1 and 8:1. In this first portion the ratio of water to alcohol remains constant. Furthermore, during this first portion of the elution compounds such as NQ & NTO are separated from the mixture.

Dining portion 1 the elation time may vary from 2-10 minutes. The time for portion 1 is defined by the elation of NTO, in that it exceeds the elation time for NTO. However the retention time of NTO will shift depending on the eluent composition, the ratio of alcohol to water. As described above, the ratio of water to alcohol may vary from 3:1 to 10:1. The adjustments to the eluent composition in portion 1 will result in retention time shifts for NQ and NTO, where smaller ratios of wafer to alcohol will result in shorter retention times.

In a second portion of the process in accordance with certain embodiments of the invention, (depleted by Roman numeral II) the ratio of water to alcohol is reduced down to a value of from about 0.8:1.0 to about 1.2:1.0. This second portion of the process in accordance with invention may be called the gradient portion. In certain embodiments of the invention RDX may be separated from the mixture towards the latter part of this gradient portion. However in other embodiments of the invention, RDX may be separated from the mixture in the third portion of the invention of the process of invention, which is described in the following paragraph. This reduction may be accomplished in a linear fashion (plotting time vs. ratio) although the process of the invention is not limited in such a manner and the ratio change may be non-linear in embodiments of the invention. During portion 2 the eluent composition changes from the parameters set in portion 1 to those set in portion 3 over 3-10 minutes.

In the third portion the process in accordance with certain embodiments of the invention, (depicted by Roman numeral III) the ratio of water to alcohol is held constant at said reduced value of from about 0.8:1.0 to about 1.2:1.0. During this third portion of the process, the conventional, or legacy explosive compounds are separated if they in fact were present in the analyzed sample.

During portion 3 the elation time may vary from 15-43 minutes. The time for portion 3 is defined by the elution of the conventional, or legacy explosive compounds, in that it exceeds the elation time for 3-nitrotoluene (3-NT) or optionally the last compound being monitored. However the retention times of the traditional explosives will shift depending on the eluent composition, the ratio of alcohol to water. The ratio of water to alcohol may vary as described above. The adjustments to the eluent composition in portion 3 will result in retention time shifts for the traditional explosive compounds, where smaller ratios of water to alcohol will result in shorter retention times.

In embodiments of the invention, there may be an additional fourth portion (depicted by Roman numeral IV) where the ratio of water to alcohol is returned back to the initial value from the first portion, such that additional analyses may be performed.

As described herein, an inventive HPLC method is described for the single column analysis of IMX constituents. The method in accordance with embodiments of the invention utilizes both an acidified mobile phase, and an acidified mobile phase gradient to separate the more hydrophilic compounds from the void volume, while maintaining the separation of the more hydrophobic compounds. The method in accordance with embodiments of the invention provides quantitative results with acceptable quality control sample results for all four of the IMX constituents. With no preparation changes, the method in accordance with embodiments of the invention also allows for simultaneous detections of the traditional explosives analyzed by US EPA method 8330.

The method in accordance with embodiments of the invention is UV and MS compatible allowing for compound confirmation by either dual column HPLC or HPLC-UV-MS analysis. In embodiments of the invention, a mass spectrometric detector may be used to reduce the likelihood of erroneous results owing to analyte ambiguity and unknown interfering compounds in complex matrixes, as well as quantification and reliable confirmation from a single analytical instrumental analysis. The use of the mass spectrometry detector also enables the possible identification of unknown compounds present in the sample that non selective detectors, such as UV absorbance detectors, docs not.

While the invention has been described in terms of some of its embodiments, those skilled in the art will recognize that the invention can be practiced with modifications within the spirit and scope of the appended claims. Thus, it is intended that all matter contained in the foregoing description or shown in the accompanying drawings shall be interpreted as illustrative rather than limiting, and the invention should be defined only in accordance with the following claims and their equivalents.

What is claimed is:

1. A liquid chromatographic method for separation of mixtures comprising at least a first explosive compound and a second explosive compound, said method comprising the steps of:
   (a) providing a sample comprising at least said first and second explosive compounds, wherein said first explosive compound is a nitroaromatic and said second explosive compound is selected from the group consisting of nitroguanidine (NQ) and nitrotriazalone (NTO),
   (b) combining said sample with an initial acidic carrier solvent to form a sample solution, said initial acidic carrier solvent comprising less than about 99 % by volume water and alcohol, acetonitrile in an amount ranging from about 0% to about 5% by volume, and 1% or less by volume of an acidic component, said initial acidic carrier solvent having an initial volume % water and a corresponding initial volume % alcohol, based upon the composition of the initial acidic carrier solvent,
   (c) passing said sample solution through a liquid chromatography column,
   (d) continuously lowering said initial volume % water to a final volume % water and a corresponding final volume % alcohol, while continuing to pass acidic carrier solvent through said liquid chromatography column, such that a solvent gradient is established during said method, and
   (e) separating said at least two explosive compounds in said column.

2. The method of claim 1 wherein said alcohol is methanol.

3. The method of claim 1 wherein said chromatographic method is high performance liquid chromatography (HPLC).

4. The method of claim 1 wherein said initial volume % water is in the range of from about 90% to about 80%, and said corresponding initial volume % alcohol is in the range of about 9% to about 19% .

5. The method of claim 4 wherein said final volume % water is in the range of from about 55% to about 45%, and said corresponding final volume % alcohol is in the range of about 44% to about 54%.

6. The method of claim 1 wherein said acidic component is selected from the group consisting of an organic acid and a halogenated organic acid.

7. The method of claim 1 further comprising a step (f) of obtaining a quantitative measurement of an amount of said explosive compounds.

8. The method of claim 6 wherein said, acidic component is trifluoroacetic acid and said acidic carrier solvent is 0.0005 to 0.0020 molar in said trifluoroacetic acid.

9. The method of claim 1 wherein said nitroaromatic is 2,4-dinitroanisole (DNAN) and said second explosive compound has multiple components, and comprises nitroguanidine (NQ) and nitrotriaxalone (NTO).

10. A liquid chromatographic method for separation of mixtures comprising at least a first explosive compound and a second explosive compound, said method comprising the steps of:
   (a) providing a sample comprising at least said first and second explosive compounds, wherein said first explosive compound is 2,4-dinitroanisole (DNAN) and said second explosive compound is selected from the group consisting of nitroguanidine (NQ) and nitrotriazalone (NTO),
   (b) combining said sample with an initial acidic carrier solvent to form a sample solution, said initial acidic carrier solvent comprising less than about 99% by volume water and alcohol, acetonitrile in an amount ranging from about 0% to about 5% by volume, and 1% or less by volume of an acidic component, said initial acidic carrier solvent having an initial volume % water and a corresponding initial volume % alcohol, based upon the composition of the initial acidic carrier solvent,
   (c) passing said sample solution through a liquid chromatography column,
   (d) continuously lowering said initial volume % water to a final volume % water and a corresponding final volume % alcohol, while continuing to pass acidic carrier solvent through said liquid chromatography column, such that a solvent gradient is established during said method, and (e) separating said at least two explosive compounds in said column.

11. The method of claim 10 wherein said alcohol is methanol.

12. The method of claim 10 wherein said chromatographic method is high performance liquid chromatography (HPLC).

13. The method of claim 10 wherein said initial volume % water is in the range of from about 90% to about 80%, and said corresponding initial volume % alcohol is in the range of about 9% to about 19%.

14. The method of claim 13 wherein said final volume % water is in the range of from about 55% to about 45%, and said corresponding final volume % alcohol is in the range of about 44% to about 54%.

15. The method of claim 10 wherein said, acidic component is selected from the group consisting of an organic acid and a halogenated organic acid.

16. The method of claim 10 further comprising a step (f) of obtaining a quantitative measurement of an amount of said explosive compounds.

17. The method of claim 15 wherein said acidic component is trifluoroacetic acid and said acidic carrier solvent is 0.0005 to 0.0020 molar in said trifluoroacetic acid.

18. The method of claim 10 wherein said second explosive compound is nitrotriazalone (NTO).

19. The method of claim 10 wherein said second explosive compound is nitroguanidine (NQ) and said sample further comprises nitrotriazalone (NTO).

20. The method of claim 18 wherein said sample further comprises hexahydro-1,3,5-trinitro-1,3,5-triazine (RDX).

* * * * *